United States Patent [19]

Abdenour

[11] 4,012,838
[45] Mar. 22, 1977

[54] METHOD FOR PRODUCING ARTIFICIAL DENTURES

[75] Inventor: Joseph D. Abdenour, Grosse Pointe, Mich.

[73] Assignee: American Denture Corporation, Scottsdale, Ariz.

[22] Filed: Jan. 30, 1975

[21] Appl. No.: 545,305

[52] U.S. Cl. .................................................. 32/2
[51] Int. Cl.² ....................................... A61C 13/00
[58] Field of Search ......................................... 32/2

[56] References Cited
UNITED STATES PATENTS

| | | | |
|---|---|---|---|
| 2,446,298 | 8/1948 | Nelson | 32/2 |
| 2,466,727 | 4/1949 | Morgan | 32/2 |
| 3,241,238 | 3/1966 | Kersten | 32/2 |
| 3,727,309 | 4/1973 | Huey | 32/2 |
| 3,839,796 | 10/1974 | Hazar | 32/2 |

*Primary Examiner*—Robert Peshock

[57] ABSTRACT

A method for producing an artificial denture comprising the production of a denture module having an assembly of prosthetic teeth with a hard U-shaped base bonded thereto and with a soft deflectably formable layer attached and adapted to be digitally formed into the human mouth whereupon it may subsequently be impression formed with an impression material comprising hard or soft liner material thereon so as to provide the conformations of a final fitting denture, and whereupon the denture thus formed conforms intimately to the edentulous areas of the human mouth. Then a first impression model is formed at one surface of the denture module, then a second impression model is formed at the other surface of the denture module in either order; then the aforementioned deflectably formable layer and impression material comprising said hard or soft liner are removed from said hard U-shaped base portion of the denture module and the hard U-shaped base remains imbedded in one of said impression models, while hard plastic denture base resins are cast against the other impression model and into bonding relation to said original hard U-shaped base to form an entire denture structure of hard character which have all of the geometry intimately to fit the edentulous area of the individual human mouth to which the original denture module was formed. It should be noted that within the context of this disclosure, that all forming methods are included such as compression moulding processes, pour fluid processes, and injection moulding processes and techniques, although diagrams presented herein relate only to compression moulding technique.

3 Claims, 4 Drawing Figures

METHOD FOR PRODUCING ARTIFICIAL DENTURES

BACKGROUND OF THE INVENTION

Prior art dentures such as those disclosed in U.S. Pat. No. 3,839,796 have been successfully produced and fitted to patients and have been very satisfactory but have included an intermediate soft deflectable layer of material between a hard U-shaped base structure and a hard liner; such soft deflectable layers have, in some instances, required a substantial amount of time to cure and become as hard as the original hard U-shaped base structure to which the assembly of teeth is affixed.

SUMMARY OF THE INVENTION

The present invention relates to a method of producing a denture partially in accordance with teachings of U.S. Pat. No. 3,839,796, but not limited thereto, and additionally, the invention comprises method steps, wherein first and second impression models are cast against the tooth and relative gum supporting sides of a denture module, whereupon the soft deflectable layer along with the attached impression material comprised of hard or soft liner material may then be stripped away from the tooth bearing hard U-shaped base assembly of the denture module so that a resin for a hard or soft plastic material may be cast between the hard U-shaped base of the denture module remaining imbeded in one impression model, while both impression models are held in a flask and compressed together, in the usual manner of flasking, so that the base of the final denture produced consists of all hard or soft materials such as hard or soft acrylic material in comparison to the hardness of the original hard U-shaped base of the aforementioned denture module, and this entire hard or soft plastic material such as acrylic is thus intimately impression contoured to the edentulous gum supporting areas of an individual human patient. Specifically, the method includes the step of producing a denture module suitable for recording the intimate contours of an individual human oral cavity and gum supporting areas, and suitable also for casting impression moulds capable of reproducing said individual intimate human oral contours; said denture module may consist of a hard U-shaped base assembly with or without metal, plastic, or wax, reinforcement materials or devices, and a soft deflectably formable layer attached permanently or temporarily thereto, either with or without plastic, metal, or wax reinforcing materials or devices, then deflectably with digital pressure, forming the soft layer to the edentulous gum area of the patient's mouth; then removing said denture module and placing impression material or hard or soft liner material on the soft deflectably formable layer so as to impression form said material in a consistency adequate to conform intimately to the details of the human mouth and allowing the impression material or hard or soft liner material to substantially cure in the patient's mouth to thereby provide a cured liner in bonded relation to the soft deflectably formed layer. The fitted module is then used to form a pair of impression models which fit intimately to the contours of the upper and lower surfaces of the fitted denture module; then the cured impression material or hard or soft liner material, along with the soft deflectably formed layer are stripped away from the hard U-shaped base assembly of the denture module, while the hard U-shaped base assembly still retained in one of the impression models and the other impression model is then positioned above the U-shaped base assembly of the denture module, allowing new hardenable denture base resin to be inserted between the hard U-shaped base assembly and the uppermost impression model so as to cast and bond a hard gum conforming structure unitarily to the hard U-shaped base assembly remaining from the denture module, whereby conformity to the intimate detail of the individual human mouth originally impression formed is achieved adjacent to said uppermost impression model.

Accordingly, it is an object of the present invention to provide an improved denture wherein a hard U-shaped assembly of prosthetic teeth are bonded to a denture base material whereupon the individually impressioned upper surface of the finished denture, or the portion which comes into intimate contact with the mucosa, is of exactly the same material as the under surfaces but which may or may not be of the same durometer hardness as the U-shaped assembly of prosthetic teeth to which said base is unitarily bonded utilizing methods and techniques pursuant to those methods and techniques as set forth herein.

Another object of the invention is to provide a method by which very accurately fitting, individually fitted, dentures may be constructed of materials individually suitable to an individual patient, and in a substantially economical manner.

Additional objects of the invention are to provide greater logistical latitude in the utilization of dentists time, whereby such efficient use of time would result in economical advantages to patients without sacrificing the quality of dentistry obtained. Objectively, utilization of the methods and techniques cited herein would provide a fast and efficient means by which a dentist could provide custom dentures to individual patients in either the usual manner, or as a chair side delivery in one day, thus providing high quality, accurately fitting, durable dentures economically.

Further objects and advantages of the invention may be apparent from the following specification, appended claims and accompanying drawings.

BRIEF DESCRIPTION OF THE DRAWINGS

FIG. 1 including the same reference characters as may be found in FIG. 14 of U.S. Pat. No. 3,839,796.

DESCRIPTION OF THE PREFERRED EMBODIMENTS

Figure 1:
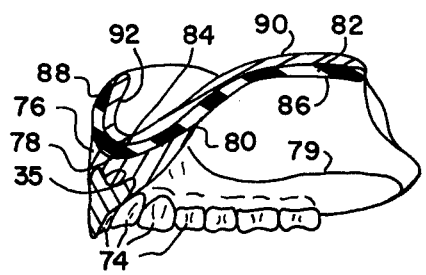
FIG. 1 is a sectional view similar to FIG. 14 of U.S. Pat. No. 3,839,796 and showing a denture similar to that disclosed therein.

As shown in FIG. 1, a denture such as disclosed in U.S. Pat. No. 3,839,796, is shown and the same reference characters and leader lines as contained in said patent are included in FIG. 1 of the drawings.

In accordance with the present invention, the denture shown in FIG. 1 is referred to as fitted denture module.

This denture module is produced in accordance with the teachings of said patent. The prosthetic teeth 74 are of hard acrylic, porcelain, silicone, or any other such suitable material, and this assembly is generally a unitary assembly held in position by plastic, metal, or wax devices or other such materials, while a hard base 76 is permanently or temporarily bonded to said assembly of teeth, the hard base 76 and teeth 74 compose a hard base assembly. This hard U-shaped base 76 is provided with a recess 78 in which a soft deflectably formable layer, with or without plastic, metal, or wax reinforcement devices attached thereto, of plastic designated 82 is bonded and this soft deflectably formable layer 88 is impression formed, with finger pressure, in an individual patient's mouth whereupon it is subsequently removed and a curable impression material or hard or soft liner material layer 90 is placed on the digitally formed soft layer 82 and reinserted into the patient's mouth so that impression forming of the impressionable liner material may take place in such a manner that the impressionable material sets up or cures in the patient's mouth to a very accurate fitting detail of the edentulous gum area. Then the denture is removed and is as shown in FIG. 1 of the drawings.

Figure 2:
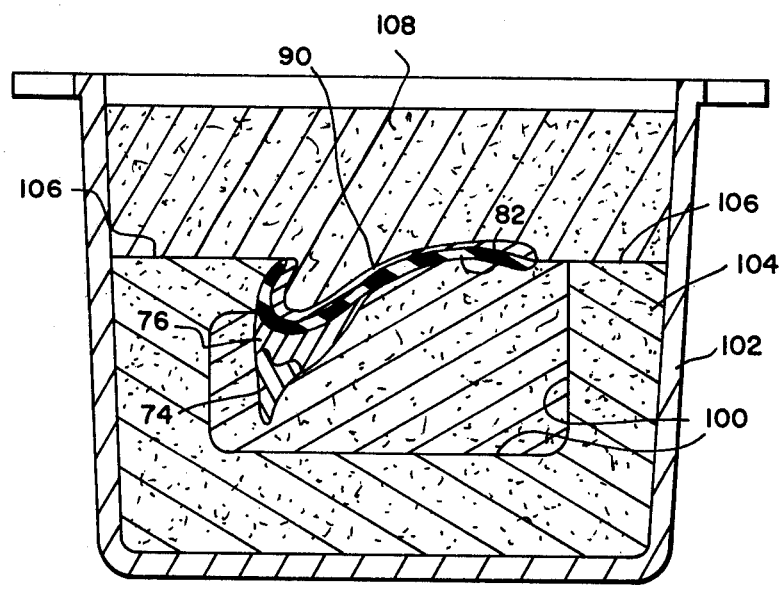
FIG. 2 is a sectional view of a dental flask with impression models cast into conformity with upper and lower surfaces of a denture module according to the present invention and as shown in FIG. 1 and showing said fitted denture module therein.
Figure 3:
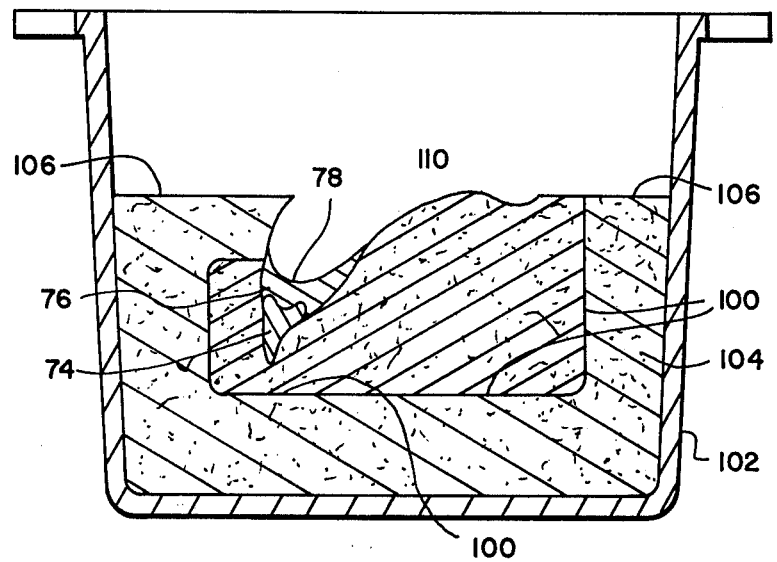
FIG. 3 is a sectional view similar to FIG. 2 but showing the upper impression model removed and the impression material or hard or soft liner material, along with the soft deflectable layer, stripped away from the fitted denture module, thus leaving the hard U-shaped assembly of prosthetic teeth in the lower most impression model held in a dental flask.

Subsequently, an impression model designated 100 in FIG. 2, is cast around the lower areas of the fitted denture module including the prosthetic teeth 74 and then the denture together with the impression model 100, is placed in a flask 102 and plaster 104 is poured in the flask around the impression model 100 up to a level 106 which subsequently forms a parting line for the impression model 100 and secondary impression model 108 as will hereinafter be described.

The impression model 100 and the plaster 104 as well as the impression model 108 are of a gypsum or plastic like material with or without metallic fillers, which may be mixed and then hardened into what is commonly known as dental stone or may be recognized as the usual mould material employed for investment casting of metals or the like.

After the plaster 104 has set up at its parting line surface 106, the upper parting line surface 106 and upper surface of the cured impressionable material liner 90 is coated with a conventional release agent and then the plaster or dental stone 108 is poured into the flask 102 over the denture and the surface 106 and the stone 108 is allowed to harden so that detail of the cured impression formed liner 90 of the denture module of FIG. 1, is transferred to the lower surface of the impression model 108 to match that originally produced on the denture module as shown in FIG. 1 by curing said impressionable material in the individual patient's mouth.

After the impression model 108 is finished and hardened, it is separated at the parting line 106 from the plaster 104 and from the upper surface of the cured liner 90, whereupon the cured line 90 and the soft deflectable layer 82 bonded thereto, may be stripped away from the hard U-shaped base assembly 76 leaving only the hard U-shaped base assembly 76 and the prosthetic teeth 74 in the impression model 100 surrounded by the hard plaster or dental stone 104. Then the U-shaped hard base assembly 76 is cleaned and exposed together with the upper surface 100 of the impression model 100 which was originally cast adjacent to the lower surface of the soft liner 82. After all appropriate surfaces have been properly treated with release agents, areas 78 and 110 are then filled or packed with a curable denture base resin designated 112 in FIG. 4 of the drawings, this material being placed in a fluid or formable state in the recess 78 and the surface 110 and this plastic material 112 being of a character comparable to the hard U-shaped base 76 which is made of hard acrylic plastic or similar suitable material, or of a character of durometer hardness when cured and at body temperature suitable to the individual requirements of individual patients with respect to the softness or hardness of the denture base material 112 in relation to the hardness of the U-shaped base 76, which is made of hard acrylic plastic or similar suitable material.

When the denture base material 112 is placed against the recess 78 and on the surface 110 the impression model 108 is placed thereover in the flask 102 and a cover 114 of the flask is compressibly closed by wing bolts 116 to compress the compression model 108 against the denture base resin 112 and to form the upper surface of the plastic 112 identical to the original surface of the cured impressionable material which recorded the contour detail of the individual patient's mouth onto surface 90, to which the finished dentures will ultimately fit.

Alternatively or preferably an ejector flask, such as that manufactured by Hanan Manufacturing Company may be compressed closed in the conventional flasking manner.

Figure 4:
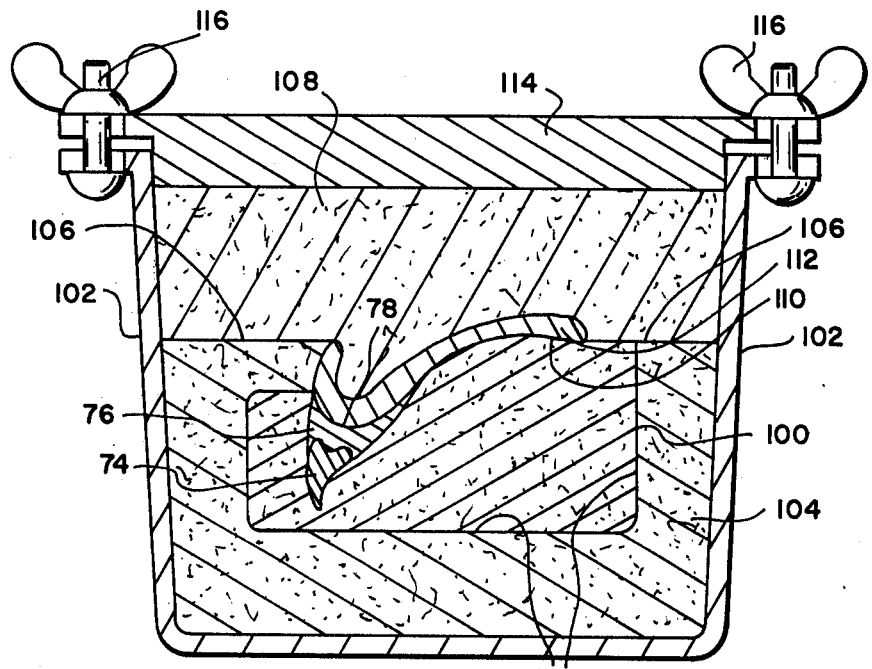
FIG. 4 is a sectional view similar to FIG. 2 showing curable denture base resin cast against the remaining hard U-shaped base assembly of the denture module held in the lower most impression model and using the upper impression model to transfer the edentulous area surface detail to the upper surface of the curable denture base resin cast and bonded to the hard U-shaped base assembly of the finished denture and showing a cover with a means for forcing the cover tight to compress the impression models together for compressibly bonding the hard plastic denture base materials to the remaining hard U-shaped base assembly of the original denture module.

After the plastic 112 has been placed in the mould between the impression models 100 and 108 as shown in FIG. 4, the plastic 112 is allowed to cure and bond to the surface 78 of the hard U-shaped assembly 76 and to harden to an ultimate consistency substantially equal to that of the hard base 76, or to varying degrees of durometer hardness or softness as is determined by the various denture base compounds suitable to these methods and techniques.

The impression models 100 and 108 are then removed from the flask 102 and are separated at the parting line 106 and the finished dentures, unitarily bonded together, including the cured base resin 112 and the hard U-shaped assembly of teeth 76 and 74, are then removed, cleaned, polished, and are ready for final delivery to the individual patient.

It must be appreciated that the various materials used in accordance with the foregoing methods may vary within the limit of equivalency as for example, the teeth 74 may be of hard acrylic, silicone, porcelain, or other suitable material, held in bonded relationship by plastic, metal, wax, rubber or other such materials used as stabilizing devices or reinforcement devices. The U-shaped base assembly may be constructed of any durometer hardness or softness a material, when cured and at body temperature. The soft deflectable liner may be of any suitable materials such as plastic, metal, wax, clay compounds, rubber compounds and the like, each with or without plastic, metal, wax or other such materials in combination. The impressionable liner 90 may be any material such as would accurately record the intimate contours of the oral cavity and gum supporting areas of the mouth; such materials as impression material or hard or soft liner material. The denture base material may be of any suitable denture base material having any of a range of durometer hardness or softness, as is dictated by the availability of such resins and the individual requirements of various individual dentists and patients.

The materials from which the impression models 100 and 108 as well as the plaster 104 are formed may be commonly known as casting stone or dental stone, or may be of other resilient or non-resilient materials such as metal, urethane, monothane, teflon and the like, and may be conventionally known to persons who use such materials for purpose of investment casting where moulds are made in accordance with the lost wax process. These methods and materials are well known to persons skilled in the art. Further, it will be understood that the pliable or soft formable portions of the denture module may include all pliable materials, either plastic, metal, wax, clay compounds, rubber compounds with or without reinforcing devices or elements, which may be comparable or equivalent in use.

The U-shaped assembly of teeth referred to herein include any tooth structure maintained in position by the use of plastic, metal, wax, clay, gypsum or other such elements; or by pre-setting such U-shaped assembly of teeth in a form wherein a formable and/or an impressionable material shall be combined to register the intimate impression of an individual patient's mouth for use in conjunction with any of the methods, or techniques disclosed herein.

Further, it should be appreciated that any materials referred to herein shall be construed to include both chemically activated resins and heat curing resins.

The method as described herein may be construed to relate to the hard liner 90 and the deflectable layer 82 in that any dental device of such character utilizing any formable or impressionable material is removed by any means from any U-shaped assembly of prosthetic teeth, (with or without plastic, metal, or wax reinforcing devices or materials), or form wherein a U-shaped assembly of prosthetic teeth is held and whereupon a permanent or temporary gum fitting structure is affixed to said U-shaped assembly for purposes of registering a relationship of the intimate contours of the human mouth of an individual to said U-shaped assembly when used in conjunction with any of the methods cited herein. The method as described herein may be also construed to include the use of matrix devices designed to register the relationship of the gum supporting areas of the oral cavity to a U-shaped assembly of teeth.

It will be appreciated that all diagrams and illustrations portray the proximal denture plate, and that all methods disclosed cited herein should be construed to include also the mandibular denture plate, in all respects.

It will be obvious to those skilled in the art that various modifications of the invention may be resorted to without departing from the spirit of the invention.

We claim:

1. A method for producing a denture comprising: forming a generally U-shaped assembly of prosthetic teeth, bonding said U-shaped assembly of teeth into a generally u-shaped hard base structure; providing a terminus of said hard base structure disposed a short distance rearwardly of the incisor areas of said assembly of prosthetic teeth; bonding a soft deflectably formable layer onto said hard U-shaped base; inserting said hard U-shaped base and deflectably formable layer into a patient's mouth and finger forming said deflectably formable layer into close proximity to the edentulous area of the patient's mouth; then removing said base and deflectably formed layer and placing a hardenable orally curable material in impressionable form on the soft deflectably formed layer; then unitarily reinserting the base and layer and curable material into the human individual's mouth and impression forming the curable impressionable material into impression conformance with said edentulous gum area of the patient's mouth and allowing the curable impressionable material to cure over the deflectably formable layer and bond thereto, to form a liner which conforms intimately to the features of the edentulous gum area of the mouth, thereby forming a fitted denture module; then making a first impression model of one side of said fitted denture module; then making a second impression model of the opposite side of said fitted denture module; then removing the impressionable material and soft deflectably formed layer from the hard U-shaped base assembly of prosthetic teeth; then casting uncured denture base resin in a formable form between said second impression model and with said first impression model with the U-shaped hard base structure imbedded therein; and allowing said uncured denture base resin to cure in bonded relationship to said hard base structure to form said denture.

2. The invention as defined in claim 1, wherein: said first impression model is inserted in a flask and plaster is poured into a mold parting surface around said denture; then coating said parting surface and said denture model with a release agent and wherein said second impression model is then cast on said release agent in said flask and over said hard liner.

3. The invention as defined in claim 2, wherein: said first and second impression models are compressed together in said flask for compression forming and bonding of said uncured hardenable plastic onto said hard base.

* * * * *